(12) United States Patent
Jouenne et al.

(10) Patent No.: US 11,841,302 B2
(45) Date of Patent: Dec. 12, 2023

(54) METHOD FOR DETERMINING THE VISCOSITY OF A POLYMER SOLUTION

(71) Applicant: Total SE, Courbevoie (FR)

(72) Inventors: Stéphane Jouenne, Bizanos (FR); Bertrand Levache, Peyrehorade (FR)

(73) Assignee: TOTAL SE, Courbevoie (FR)

( * ) Notice: Subject to any disclaimer, the term of this patent is extended or adjusted under 35 U.S.C. 154(b) by 111 days.

(21) Appl. No.: 17/432,009

(22) PCT Filed: Feb. 19, 2019

(86) PCT No.: PCT/IB2019/000194
§ 371 (c)(1),
(2) Date: Aug. 18, 2021

(87) PCT Pub. No.: WO2020/169999
PCT Pub. Date: Aug. 27, 2020

(65) Prior Publication Data
US 2022/0155201 A1    May 19, 2022

(51) Int. Cl.
*G01N 11/00* (2006.01)
*G01N 11/02* (2006.01)
*G01N 33/44* (2006.01)

(52) U.S. Cl.
CPC ........... *G01N 11/02* (2013.01); *G01N 33/442* (2013.01); *G01N 2011/004* (2013.01); *G01N 2011/0033* (2013.01)

(58) Field of Classification Search
CPC ................ G01N 11/02; G01N 33/442; G01N 2011/0033; G01N 2011/004; G01N 11/00; G01N 2011/006; G01N 2001/0026
USPC .... 73/54.37, 54.23; 702/22, 25, 27, 127, 85, 702/179, 189, 199
See application file for complete search history.

(56) References Cited

U.S. PATENT DOCUMENTS 4,814,096 A    3/1989    Evani

FOREIGN PATENT DOCUMENTS

WO    2020/169999 A1    8/2020

OTHER PUBLICATIONS

International Search Report and Written Opinion for International Application No. PCT/IB2019/000194, entitled "Method for Determining the Viscosity of a Polymer Solution," consisting of 8 pages, dated Oct. 29, 2019.

(Continued)

*Primary Examiner* — Robert R Raevis
(74) *Attorney, Agent, or Firm* — Hamilton, Brook, Smith & Reynolds, P.C.

(57) ABSTRACT

The invention relates to a method for determining the intrinsic viscosity [η] of an aqueous polymer solution at a temperature T, wherein the aqueous polymer solution comprises at least one acrylamide-based polymer in an aqueous solvent, the aqueous solvent having a salinity of from 6 to 250 g/L, the method comprising the steps of: —providing a single universal relation $R_1$ between (i), the product of polymer concentration and intrinsic viscosity C·[η], and (ii) specific viscosity at zero shear rate $\eta_{sp}$; —performing a measurement of the dynamic viscosity of the aqueous polymer solution at one polymer concentration $C_1$, at temperature T and at various shear rates; —determining from said measurement the zero-shear viscosity $\eta_0$ of the aqueous polymer solution at polymer concentration $C_1$ and at temperature T; —calculating the specific viscosity at zero shear rate of the aqueous polymer solution at polymer concentration C and at temperature T as $\eta_{sp}=(\eta_0-\eta_s)/\eta_s$, where $\eta_s$ is the zero-shear viscosity of the aqueous solvent; —estimating the intrinsic viscosity [η] of the aqueous polymer solution at temperature T by applying the universal relation $R_1$ to the calculated specific viscosity at zero shear rate $\eta_{sp}$ and polymer concentration $C_1$.

20 Claims, 4 Drawing Sheets

(56) References Cited

OTHER PUBLICATIONS

Abdel-Azim A., et al. "Determination of intrinsic viscosity of polymeric compounds through a single specific viscosity measurement," Polymer, Elsevier Science Publishers B.V, GB, vol. 39, No. 26, pp. 6827-6833 (Feb. 20, 1998).

Bouldin M., et al., "Prediction of the non-Newtonian viscosity and shear stability of polymer solutions," Colloid and Polymer Science, vol. 266, No. 9, pp. 793-805 (Apr. 1988).

Szopinski D., et al. "Structure-property relationships of carboxymethyl hydroxypropyl guar gum in water and a hyperentanglement parameter," Carbohydrate Polymers 119, pp. 159-166, Elsevier Ltd. (http://dx.doi.org/10.1016/j.carbpol.2014.11.050) (2015).

Kulicke W., et al. "Description and Forecast of Rheological Characteristics of Semi-Dilute Polymer Solutions as a Function of the Molecular Weight, Concentration and Solvent Quality," Polymer News, vol. 16, pp. 39-48, Gordon and Breach Science Publishers S.A. (1991).

Grigorescu G., et al., "Prediction of Viscoelastic Properties and Shear Stability of Polymers in Solution," Advances in Polymer Science, vol. 152, Spring-Verlag Berlin Heideberg (doi.org/10.1007/3-540-46778-5_1) (2000).

Kulicke W., et al., "The shear viscosity dependence on concentration, molecular weight, and shear rate of polystyrene solutions," Rheol Acta vol. 23, No. 1, pp. 75-83 (doi.org/10.1007/BF01333878) (1984).

Tam, K. C., et al. "Comments on the Accuracy of Zero Shear Intrinsic Viscosity of High Molecular Weight Polyacrylamide", Polymer International 24 (1991) 15-22.

METHOD FOR DETERMINING THE VISCOSITY OF A POLYMER SOLUTION

This application is the U.S. National Stage of International Application No. PCT/IB2019/000194, filed Feb. 19, 2019, which designates the U.S. and was published in English. The entire teachings of the above application are incorporated herein by reference.

TECHNICAL FIELD

The present invention relates to a method for determining the intrinsic viscosity of a polymer solution comprising at least one acrylamide-based polymer.

TECHNICAL BACKGROUND

Hydrocarbons (such as crude oil) are extracted from a subterranean formation (or reservoir) by means of one or more production wells drilled in the reservoir. Before production begins, the formation, which is a porous medium, is saturated with hydrocarbons.

The initial recovery of hydrocarbons is generally carried out by techniques of "primary recovery", in which only the natural forces present in the reservoir are relied upon. In this primary recovery, only part of the hydrocarbons is ejected from the pores by the pressure of the formation. Typically, once the natural forces are exhausted and primary recovery is completed, there is still a large volume of hydrocarbons left in the reservoir.

This phenomenon has led to the development of enhanced oil recovery (EOR) techniques. Many of such EOR techniques rely on the injection of a fluid into the reservoir in order to produce an additional quantity of hydrocarbons.

The fluid used can in particular be an aqueous solution ("waterflooding process"), such as brine, which is injected via one or more injection wells in order to maintain reservoir pressure and push the oil from the pores.

Large amounts of water can also be recovered from the production wells. This is called "produced water". The produced water can be e.g. discharged to the environment (after treatment) or reinjected into the subterranean formation via the injection wells.

A polymer (for example an acrylamide-based polymer) can also be added to the water to increase its viscosity and increase its sweep efficiency in recovering hydrocarbons ("polymer flooding process"). In this case, the produced water contains part of the polymer, which can thus be recovered.

However, depending on the conditions inside the subterranean formation (temperature, salinity, permeability), the nature of the polymer (monomer composition, molecular weight) must be adapted, in order to be able to achieve a proper viscosification of the water used for the polymer flooding and ensure good propagation in the porous medium. The viscosity of a polymer depends on a number of factors such as the type of polymer, the composition of the polymer, the concentration of the polymer, the molecular weight of the polymer (which decreases when the polymer is degraded upon use), the distribution of its molecular weight, the salinity of the subterranean formation, the temperature of the subterranean formation, the shear rate at which the viscosity is measured.

Furthermore, an estimation of the viscosity of a polymer under the conditions of the subterranean formation is often necessary in order to characterize the polymer, to perform quality controls on the polymers or the polymer solutions used in the subterranean formations, or to provide data for studies, design of equipment or simulation procedures for estimating the incremental oil recovered. Nevertheless, until now the estimation of the viscosity of a polymer has been a difficult, expensive and long procedure which requires a series of steps, measurements and experiments which are complex, time consuming and sometimes inaccurate.

The article of Bouldin M. et al. (*Prediction of the non-Newtonian viscosity and shear stability of polymer solutions*), 1988 (doi.org/10.1007/BF01417863) relates to the prediction of the zero-shear viscosity and the shear rate dependent viscosity by using structure-property relationships.

The article of Szopinski D. et al. (*Structure-property relationships of carboxymethyl hydroxypropyl guar gum in water and a hyperentanglement parameter*), 2015, (doi.org/10.1016/j.carbpol.2014.11.050) describes the determination of the viscoelastic properties of carboxymethyl hydroxypropyl guar gum in aqueous solution as a function of concentration and molecular weight, using SEC/MALLS/dRI and viscometry.

The article of Kulicke W.-M. et al. (*Description and forecast of rheological characteristics of semi-dilute polymer solutions as a function of the molecular weight, concentration and solvent quality*), 1991 (Polymer News, volume 16, pages 39-48) describes the rheological properties which enable the prediction of the flow behavior of semi-dilute polymer solutions from a molecular point of view. By using scaling laws, it is possible to predict elastic and viscous characteristics with respect to molecular parameters.

The article of Grigorescu G. et. al. (*Prediction of viscoelastic properties and shear stability of polymers in solution*), 2000 (doi.org/10.1007/3-540-46778-5_1) describes the possibilities of predicting the viscoelastic properties and the shear stability using the entanglement and reputation concepts and exemplifying mainly with narrow distributed polystyrene samples.

The article of Kulicke W.-M. et al. (*The shear viscosity dependence on the concentration, molecular weight, and shear rate of polystyrene solutions*), 1984 (doi.org/10.1007/BF01333878) relates to the solution viscosity of narrow molecular weight distribution polystyrene samples dissolved in toluene and trans-decalin. In this article, the effect of polymer concentration, molecular weight and shear rate on viscosity was determined.

There is thus a need for a method for determining the viscosity of an aqueous polymer solution, notably a polymer solution comprising an acrylamide-based polymer, in a variety of conditions, in an easy, rapid and cost-effective manner. There is also a need for a method for determining the molecular weight of an acrylamide-based polymer without performing any complex and lengthy measurements.

SUMMARY OF THE INVENTION

It is a first object of the invention to provide a method for determining the intrinsic viscosity $[\eta]$ of an aqueous polymer solution at a temperature T, wherein the aqueous polymer solution comprises at least one acrylamide-based polymer in an aqueous solvent, the aqueous solvent having a salinity of from 6 to 250 g/L, the method comprising the steps of:

providing a single universal relation $R_1$ between (i), the product of polymer concentration and intrinsic viscosity $C \cdot [\eta]$, and (ii) specific viscosity at zero shear rate $\eta_{sp}$;

performing a measurement of the dynamic viscosity of the aqueous polymer solution at one polymer concentration $C_1$, at temperature T and at various shear rates;

determining from said measurement the zero-shear viscosity $\eta_0$ of the aqueous polymer solution at polymer concentration $C_1$ and at temperature T;

calculating the specific viscosity at zero shear rate of the aqueous polymer solution at polymer concentration $C_1$ and at temperature T as $\eta_{sp} = (\eta_0 - \eta_s)/\eta_s$, where $\eta_s$ is the zero-shear viscosity of the aqueous solvent;

estimating the intrinsic viscosity $[\eta]$ of the aqueous polymer solution at temperature T by applying the universal relation $R_1$ to the calculated specific viscosity at zero shear rate $\eta_{sp}$ and polymer concentration $C_1$.

In some variations, one or more measurements of the dynamic viscosity of the aqueous polymer solution at various shear rates are performed only at the single polymer concentration $C_1$.

In some variations, the method comprises:

performing measurements of the dynamic viscosity of the aqueous polymer solution, at at least two polymer concentrations $C_1$ and $C_2$, at temperature T, and at various shear rates;

determining from said measurements the zero-shear viscosity $\eta_0$ of the aqueous polymer solution at the various polymer concentrations and at temperature T;

calculating the specific viscosity at zero shear rate of the aqueous polymer solution at the various polymer concentrations and at temperature T as $\eta_{sp} = (\eta_0 - \eta_s)/\eta_s$, where $\eta_s$ is the zero-shear viscosity of the aqueous solvent;

estimating an average intrinsic viscosity $[\eta]$ of the aqueous polymer solution at temperature T by fitting the calculated specific viscosity at zero shear rate of the aqueous polymer solution at the various polymer concentrations and at temperature T with the universal relation $R_1$.

In some variations, the single universal relation $R_1$ is obtained by:

providing a number of acrylamide-based polymers;

for each acrylamide-based polymer, performing several measurements of the dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving the specific viscosity at zero shear rate and intrinsic viscosity of each aqueous solution, at each concentration and temperature, from said measurements, so as to obtain a set of specific viscosity at zero shear rate data associated with product of intrinsic viscosity and polymer concentration data;

providing a mathematical fit for the specific viscosity at zero shear rate data as a function of the product of intrinsic viscosity and polymer concentration data.

In some variations, the single universal relation $R_1$ is defined as $\eta_{sp} = C \cdot [\eta] + 0.56 (C \cdot [\eta])^{2.17} + 0.0026 (C \cdot [\eta])^{4.72}$ or as any other function where $\eta_{sp}$ deviates from $C \cdot [\eta] + 0.56 (C \cdot [\eta])^{2.17} + 0.0026 (C \cdot [\eta])^{4.72}$ at any value of $C \cdot [\eta]$ by less than 20%, preferably by less than 10%, more preferably by less than 5%.

The invention also relates to a method for determining the dynamic viscosity of an aqueous polymer solution as a function of shear rate, at a temperature T and at a polymer concentration C', wherein the aqueous polymer solution comprises at least one acrylamide-based polymer in an aqueous solvent, the aqueous solvent having a salinity of from 6 to 250 g/L, the method comprising:

providing a single universal relation $R_2$ between (i) the product of polymer concentration and intrinsic viscosity $C \cdot [\eta]$ and (ii) Carreau coefficient n;

providing a single universal relation $R_3$ between (i) the product of polymer concentration and intrinsic viscosity $C \cdot [\eta]$ and (ii) the ratio of relaxation time to diluted regime-relaxation time $\lambda/\lambda_d$;

determining the intrinsic viscosity $[\eta]$ of the aqueous polymer solution at temperature T according to the method described above, wherein the one or more measurements of the dynamic viscosity of the aqueous polymer solution is/are performed at one or more polymer concentrations other than C';

estimating the diluted regime-relaxation time $\lambda_d$ of the aqueous polymer solution at temperature T by:

determining the relaxation time $\lambda_1$ of the aqueous polymer solution at temperature T and at a single polymer concentration $C_1$, from the measurement of the dynamic viscosity of the aqueous polymer solution at polymer concentration $C_1$ and at temperature T, and then applying the universal relation $R_3$ to the determined relaxation time $\lambda_1$, polymer concentration $C_1$ and the determined intrinsic viscosity $[\eta]$ at temperature T; or determining at least two relaxation times $\lambda_1$ and $\lambda_2$ of the aqueous polymer solution at temperature T and at at least two respective polymer concentrations $C_1$ and $C_2$, from respective measurements of the dynamic viscosity of the aqueous polymer solution at the at least two polymer concentrations $C_1$ and $C_2$ and at temperature T, and applying the universal relation $R_3$ to the at least two determined relaxation time $\lambda_1$ and $\lambda_2$, respective polymer concentration $C_1$ and $C_2$ and the determined intrinsic viscosity $[\eta]]$ at temperature T so as to provide an average value of $\lambda_d$ at temperature T;

estimating the relaxation time $\lambda'$ of the aqueous polymer solution at temperature T and polymer concentration C' by applying the universal relation $R_3$ to the estimated diluted-regime relaxation time $\lambda_d$, the polymer concentration C' and the determined intrinsic viscosity $[\eta]$ at temperature T;

estimating the Carreau coefficient n' of the aqueous polymer solution at temperature T and polymer concentration C' by applying the universal relation $R_2$ to polymer concentration C' and intrinsic viscosity $[\eta]$ at temperature T;

estimating the specific viscosity at zero shear rate $\eta_{sp}'$ of the aqueous polymer solution at polymer concentration C' and at temperature T by applying the universal relation $R_1$ to the determined intrinsic viscosity $[\eta]$ at temperature T and polymer concentration C';

estimating the zero-shear viscosity $\eta_0'$ of the aqueous polymer solution at polymer concentration C' and at temperature T as $\eta_0' = \eta_s \cdot (\eta_{sp}' + 1)$;

estimating the dynamic viscosity $\eta'$ of the aqueous polymer solution as a function of shear rate $\dot{\gamma}$, at temperature T and at polymer concentration C' by applying Carreau's equation: $\eta' = \eta_s + (\eta_0' - \eta_s) \cdot [1 + (\lambda' \cdot \dot{\gamma})^2]^{(n'-1)/2}$.

In some variations, the single universal relation $R_2$ is obtained by:

providing a number of acrylamide-based polymers;

for each acrylamide-based polymer, performing several measurements of the dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving the Carreau coefficient and intrinsic viscosity of each aqueous solution, at each concentration and temperature, from said measurements, so as to obtain a set of Carreau coefficient data associated with product of intrinsic viscosity and polymer concentration data;

providing a mathematical fit for the Carreau coefficient data as a function of the product of intrinsic viscosity and polymer concentration data.

In some variations, the single universal relation $R_2$ is defined as $n=1-(0.796-0.687\times\exp(-0.059\times C\cdot[\eta])$ or as any other function where n deviates from $1-(0.796-0.687\times\exp(-0.059\times C\cdot[\eta])$ at any value of $C\cdot[\eta]$ by less than 20%, preferably by less than 10%, more preferably by less than 5%.

In some variations, the single universal relation $R_3$ is obtained by:

providing a number of acrylamide-based polymers;

for each acrylamide-based polymer, performing several measurements of the dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving the relaxation time, diluted regime-relaxation time and intrinsic viscosity of each aqueous solution, at each concentration and temperature, from said measurements, so as to obtain a set of relaxation time-to-diluted regime-relaxation time ratio data associated with product of intrinsic viscosity and polymer concentration data;

providing a mathematical fit for the relaxation time-to-diluted regime-relaxation time ratio data as a function of the product of intrinsic viscosity and polymer concentration data.

In some variations, the single universal relation $R_3$ is defined as $\lambda/\lambda_d=1+0.04 \, (C\cdot[\eta])^{2.4}$ or as any other function where $\lambda/\lambda_d$ deviates from $1+0.04 \, (C\cdot[\eta])^{2.4}$ at any value of $C\cdot[\eta]$ by less than 20%, preferably by less than 10%, more preferably by less than 5%.

In some variations, the one or more measurements of the dynamic viscosity of the aqueous polymer solution is/are performed at one or more polymer concentrations C such that $C\cdot[\eta]$ is within the range of 1 to 10 and $C'\cdot[\eta]$ is out of the range of 1 to 10; and preferably $C\cdot[\eta]$ is within the range of 2 to 5 and $C'\cdot[\eta]$ is out of the range of 2 to 5.

The invention also relates to a method for determining the dynamic viscosity of an aqueous polymer solution as a function of shear rate, at a temperature T' and at a polymer concentration C', wherein the aqueous polymer solution comprises at least one acrylamide-based polymer in an aqueous solvent, the aqueous solvent having a salinity of from 6 to 250 g/L, the method comprising:

providing a single universal relation $R_2$ between (i) the product of polymer concentration and intrinsic viscosity $C\cdot[\eta]$ and (ii) Carreau coefficient n;

providing a single universal relation $R_3$ between (i) the product of polymer concentration and intrinsic viscosity $C\cdot[\eta]$ and (ii) the ratio of relaxation time to diluted regime-relaxation time $\lambda/\lambda_d$;

determining the intrinsic viscosity $[\eta]$ of the aqueous polymer solution at a plurality of temperatures T different from T', wherein each determination of the intrinsic viscosity is performed according to the method described above;

evaluating the intrinsic viscosity $[\eta]$ of the aqueous polymer solution at temperature T' based on the determined intrinsic viscosity $[\eta]$ of the aqueous polymer solution at the plurality of temperatures T, by a mathematical fit;

estimating the diluted regime-relaxation time $\lambda_d$ of the aqueous polymer solution at one or more temperatures T by:

determining the relaxation time $\lambda_1$ of the aqueous polymer solution at a temperature T and at a polymer concentration $C_1$, from the measurement of the dynamic viscosity of the aqueous polymer solution at polymer concentration $C_1$ and at said temperature T, and then applying the universal relation $R_3$ to the determined relaxation time $\lambda_1$, polymer concentration $C_1$ and the determined intrinsic viscosity $[\eta]$ at this temperature T; or determining at least two relaxation times $\lambda_1$ and $\lambda_2$ of the aqueous polymer solution at temperature T and at at least two respective polymer concentrations $C_1$ and $C_2$, from respective measurements of the dynamic viscosity of the aqueous polymer solution at the at least two polymer concentrations $C_1$ and $C_2$ and at temperature T, and applying the universal relation $R_3$ to the at least two determined relaxation time $\lambda_1$ and $\lambda_2$, respective polymer concentration $C_1$ and $C_2$ and the determined intrinsic viscosity $[\eta]]$ at temperature T so as to provide an average value of $\lambda_d$ at temperature T;

estimating the diluted regime-relaxation time $\lambda_d$ of the aqueous polymer solution at temperature T' as:

$$\lambda_d(T')\times(\eta_s(T')\times[\eta](T')\times T)/(\eta_s(T)\times[\eta](T)\times T')$$

where $\lambda_d(T')$ is the diluted regime-relaxation time $\lambda_d$ of the aqueous polymer solution at temperature T, $\eta_s(T')$ and $\eta_s(T)$ are respectively the zero-shear viscosities of the aqueous solvent at temperatures T' and T, and $[\eta](T')$ and $[\eta](T)$ are respectively the intrinsic viscosities of the aqueous polymer solution at temperatures T' and T;

estimating the relaxation time $\lambda'$ of the aqueous polymer solution at temperature T' and polymer concentration C' by applying the universal relation $R_3$ to the estimated dilute-regime relaxation time $\lambda_d$ at temperature T', the polymer concentration C' and the evaluated intrinsic viscosity $[\eta]$ at temperature T';

estimating the Carreau coefficient n' of the aqueous polymer solution at temperature T' and polymer concentration C' by applying the universal relation $R_2$ to polymer concentration C' and the evaluated intrinsic viscosity $[\eta]$ at temperature T';

estimating the specific viscosity at zero shear rate $\eta_{sp}'$ of the aqueous polymer solution at polymer concentration C' and at temperature T' by applying the universal relation $R_1$ to the evaluated intrinsic viscosity $[\eta]$ at temperature T' and polymer concentration C';

estimating the zero-shear viscosity $\eta_0'$ of the aqueous polymer solution at polymer concentration C' and at temperature T' as $\eta_0'=\eta_s\cdot(\eta_{sp}'+1)$;

estimating the dynamic viscosity $\eta'$ of the aqueous polymer solution as a function of shear rate $\dot{\gamma}$, at temperature T' and at polymer concentration C' by applying Carreau's equation: $\eta'=\eta_s+(\eta_0'-\eta_s)\cdot[1+(\lambda'\cdot\dot{\gamma})^2]^{(n'-1)/2}$.

In some variations, the single universal relation $R_2$ is obtained by:

providing a number of acrylamide-based polymers;

for each acrylamide-based polymer, performing several measurements of the dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving the Carreau coefficient and intrinsic viscosity of each aqueous solution, at each concentration and temperature, from said measurements, so as to obtain a set of Carreau coefficient data associated with product of intrinsic viscosity and polymer concentration data;

providing a mathematical fit for the Carreau coefficient data as a function of the product of intrinsic viscosity and polymer concentration data.

In some variations, the single universal relation $R_2$ is defined as $n=1-(0.796-0.687 \times \exp(-0.059 \times C \cdot [\eta]))$ or as any other function where n deviates from $1-(0.796-0.687 \times \exp(-0.059 \times C \cdot [\eta]))$ at any value of $C \cdot [\eta]$ by less than 20%, preferably by less than 10%, more preferably by less than 5%.

In some variations, the single universal relation $R_3$ is obtained by:

providing a number of acrylamide-based polymers;

for each acrylamide-based polymer, performing several measurements of the dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving the relaxation time, diluted regime-relaxation time and intrinsic viscosity of each aqueous solution, at each concentration and temperature, from said measurements, so as to obtain a set of relaxation time-to-diluted regime-relaxation time ratio data associated with product of intrinsic viscosity and polymer concentration data;

providing a mathematical fit for the relaxation time-to-diluted regime-relaxation time ratio data as a function of the product of intrinsic viscosity and polymer concentration data.

In some variations, the single universal relation $R_3$ is defined as $\lambda/\lambda_d=1+0.04(C \cdot [\eta])^{2.4}$ or as any other function where $\lambda/\lambda_d$ deviates from $1+0.04(C \cdot [\eta])^{2.4}$ at any value of $C \cdot [\eta]$ by less than 20%, preferably by less than 10%, more preferably by less than 5%.

The invention also relates to a method for determining the viscosimetric molecular weight of an acrylamide-based polymer, the method comprising:

providing at least one aqueous polymer solution, the aqueous polymer solution comprising the polymer in an aqueous solvent, the aqueous solvent having a salinity of from 6 to 250 g/L;

providing a single universal relation $R_3$ between (i) the product of polymer concentration and intrinsic viscosity $C \cdot [\eta]$ and (ii) the ratio of relaxation time to diluted regime-relaxation time $\lambda/\lambda_d$;

determining the intrinsic viscosity $[\eta]$ of the aqueous polymer solution at a temperature T according to the method described above;

estimating the diluted regime-relaxation time $\lambda_d$ of the aqueous polymer solution at temperature T by:

determining the relaxation time $\lambda_1$ of the aqueous polymer solution at temperature T and polymer concentration $C_1$, from the measurement of the dynamic viscosity of the aqueous polymer solution at polymer concentration $C_1$ and at temperature T, and then applying the universal relation $R_3$ to the determined relaxation time $\lambda_1$, polymer concentration $C_1$ and the determined intrinsic viscosity $[\eta]$ at temperature T; or determining at least two relaxation times $\lambda_1$ and $\lambda_2$ of the aqueous polymer solution at temperature T and at at least two respective polymer concentrations $C_1$ and $C_2$, from respective measurements of the dynamic viscosity of the aqueous polymer solution at the at least two polymer concentrations $C_1$ and $C_2$ and at temperature T, and applying the universal relation $R_3$ to the at least two determined relaxation time $\lambda_1$ and $\lambda_2$, respective polymer concentration $C_1$ and $C_2$ and the determined intrinsic viscosity $[\eta]$ at temperature T so as to provide an average value of $\lambda_d$ at temperature T;

estimating the molecular weight of the polymer according to the equation $M=(\lambda_d \cdot T)/([\eta] \cdot \eta_s)/1.474$ where $\eta_s$ is the zero-shear viscosity of the aqueous solvent at temperature T.

In some variations, the single universal relation $R_3$ is obtained by:

providing a number of acrylamide-based polymers;

for each acrylamide-based polymer, performing several measurements of the dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving the relaxation time, diluted regime-relaxation time and intrinsic viscosity of each aqueous solution, at each concentration and temperature, from said measurements, so as to obtain a set of relaxation time-to-diluted regime-relaxation time ratio data associated with product of intrinsic viscosity and polymer concentration data;

providing a mathematical fit for the relaxation time-to-diluted regime-relaxation time ratio data as a function of the product of intrinsic viscosity and polymer concentration data.

In some variations, the single universal relation $R_3$ is defined as $\lambda/\lambda_d=1+0.04(C \cdot [\eta])^{2.4}$ or as any other function where $\lambda/\lambda_d$ deviates from $1+0.04(C \cdot [\eta])^{2.4}$ at any value of $C \cdot [\eta]$ by less than 20%, preferably by less than 10%, more preferably by less than 5%.

In some variations of any of the above methods, the polymer comprises units derived from one or more monomers selected from acrylamide, sodium acrylate, N-vinyl pyrrolidone and 2-acrylamide-2-methylpropane sulfonate, and wherein the polymer is preferably selected from the homopolymer of 2-acrylamide-2-methylpropane sulfonate, copolymers of acrylamide and sodium acrylate, copolymers of acrylamide and 2-acrylamide-2-methylpropane sulfonate, copolymers of acrylamide and N-vinyl pyrrolidone, terpolymers of acrylamide, sodium acrylate and N-vinyl pyrrolidones and terpolymers of acrylamide, sodium acrylate and 2-acrylamide-2-methylpropane sulfonate.

The present invention makes it possible to address the need expressed above. In particular, the invention provides a method for determining the viscosity of an aqueous polymer solution, notably a polymer solution comprising an acrylamide-based polymer, in a variety of conditions, in an easy, rapid and cost-effective manner. The invention also provides a method for determining the molecular weight of an acrylamide-based polymer without performing any complex and lengthy measurements.

The invention relies on the surprising finding by the inventors that acrylamide-based polymers in aqueous solutions having a salinity between 6 and 250 g/L behave according to a number of universal relations, which are valid for any polymer in this family, in a large variety of conditions. This makes it possible to predict a number of useful properties of a polymer solution based on a very limited set of measurements on the polymer.

In particular, a single universal relation $R_1$ between the product of polymer concentration and intrinsic viscosity, and the specific viscosity at zero shear rate of these polymer solutions has been found. By using this relation, the intrinsic viscosity of the polymer may be determined for a wide range of concentrations and temperatures, without carrying out complex measurements for each concentration of polymer. The determination of this intrinsic viscosity makes it possible in turn, using further universal relations, to determine other parameters such as the dynamic viscosity of a polymer solution in any set of conditions, or even the molecular weight of the polymer.

DESCRIPTION OF EMBODIMENTS

Figure 1:
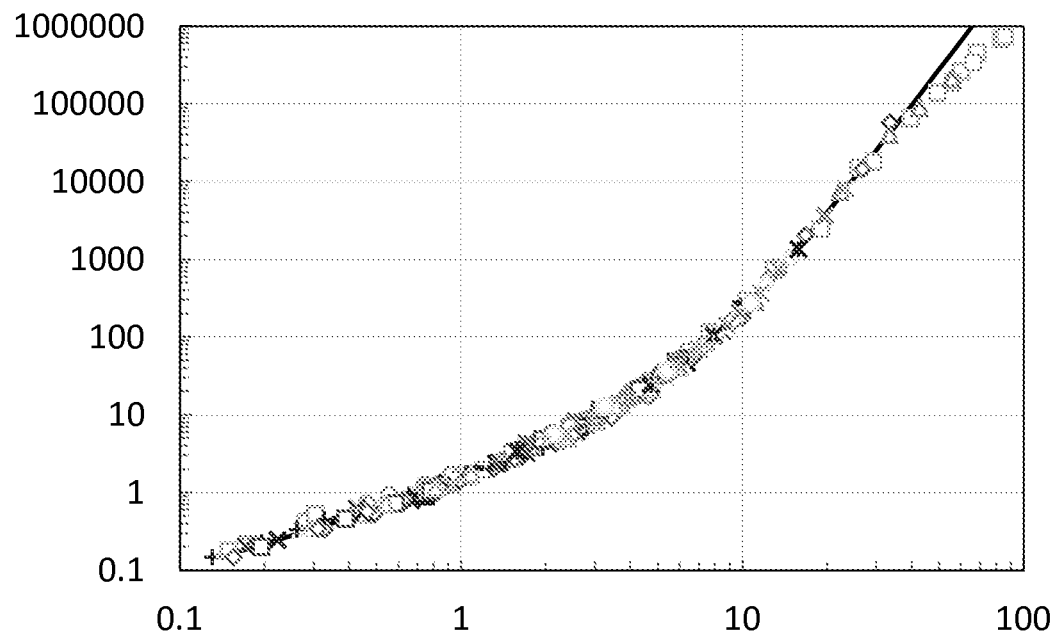
FIG. 1 shows the specific viscosity at zero shear rate $\eta_{sp}$ of a polymer as a function of the product of the polymer concentration and the intrinsic viscosity, for a large number of samples. The dimensionless specific viscosity at zero shear rate can be read on the Y-axis and the dimensionless product of the polymer concentration and the intrinsic viscosity can be read on the X-axis.

The invention will now be described in more detail without limitation in the following description.

Polymer Solution

The polymer solution referred to in the present application comprises at least one acrylamide-based polymer in an aqueous solvent.

The acrylamide-based polymer may comprise units derived from one or more monomers selected from acrylamide, sodium acrylate, N-vinyl pyrrolidone and 2-acrylamide-2-methylpropane sulfonate. Preferably the polymer is selected from the homopolymer of 2-acrylamide-2-methylpropane sulfonate, copolymers of acrylamide and sodium acrylate, copolymers of acrylamide and 2-acrylamide-2-methylpropane sulfonate, copolymers of acrylamide and N-vinyl pyrrolidone, terpolymers of acrylamide, sodium acrylate and N-vinyl pyrrolidone and terpolymers of acrylamide, sodium acrylate and 2-acrylamide-2-methylpropane sulfonate.

According to some embodiments, only one acrylamide-based polymer is present in the polymer solution.

According to other embodiments, more than one acrylamide-based polymers, for example two, or three, or four, or more than four acrylamide-based polymers are present in the polymer solution.

The polyamide polymer(s) may be present in the polymer solution at a concentration from 20 to 20000 ppm by weight and preferably from 50 to 17000 ppm by weight. For example, the polyamide polymer(s) may be present in the polymer solution at a concentration from 20 to 50 ppm; or from 50 to 100 ppm; or from 100 to 200 ppm; or from 200 to 500 ppm; or from 500 to 1000 ppm; or from 1000 to 1500 ppm; or from 1500 to 2000 ppm; or from 2000 to 2500 ppm; or from 2500 to 3000 ppm; or from 3000 to 3500 ppm; or from 3500 to 4000 ppm; or from 4000 to 4500 ppm; or from 4500 to 5000 ppm; or from 5000 to 5500 ppm; or from 5500 to 6000 ppm; or from 6000 to 6500 ppm; or from 6500 to 7000 ppm; or from 7000 to 7500 ppm; or from 7500 to 8000 ppm; or from 8000 to 8500 ppm; or from 8500 to 9000 ppm; or from 9000 to 9500 ppm; or from 9500 to 10000 ppm by weight.

The aqueous solvent in which the acrylamide-based polymer is dissolved may be or may derive from produced water, fresh water, sea water or aquifer water.

The aqueous solvent has a salinity from 6 to 250 g/L. For example, the aqueous solvent may have a salinity from 6 to 10 g/L; or from 10 to 20 g/L; or from 20 to 30 g/L; or from 30 to 40 g/L; or from 40 to 50 g/L; or from 50 to 60 g/L; or from 60 to 70 g/L; or from 70 to 80 g/L; or from 80 to 90 g/L; or from 90 to 100 g/L; or from 100 to 120 g/L; or from 120 to 140 g/L; or from 140 to 160 g/L; or from 160 to 180 g/L; or from 180 to 200 g/L; or from 200 to 220 g/L; or from 220 to 240 g/L; or from 240 to 250 g/L. Salinity is defined herein as the total concentration of dissolved inorganic salts in water, including e.g. NaCl, $CaCl_2$, $MgCl_2$ and any other inorganic salts.

The polymer solution may further comprise additives such as surfactants, salts, sacrificial agents, pH adjustment agents, solvents and/or marking agents.

The polymer solution according to the invention may be used in a hydrocarbon recovery process, and more preferably in an enhanced oil recovery process. The polymer solution may therefore be injected into a subterranean formation via one or more injection wells.

The temperature within the subterranean formation may range from 25 to 140° C., preferably from 40 to 140° C. and more preferably from 50 to 120° C.

The injection of the polymer solution may be performed at a pressure from 30 to 1000 bar, preferably from 50 to 350 bar.

The permeability of at least a portion of the subterranean formation may range from 2 to 20000 md, preferably from 10 to 20000 md and more preferably from 100 to 10000 md, as estimated by well log.

Method for Determining the Intrinsic Viscosity of a Polymer Solution

The invention first relates to a method for determining the intrinsic viscosity $[\eta]$ of the polymer solution described above, at a given temperature T.

Unless specified otherwise, by "viscosity" $\eta$ of a polymer solution is meant herein the dynamic viscosity of a polymer solution. The viscosity of the polymer solution depends on the applied shear rate, and physicochemical conditions such as the nature of the polymer, molecular weight of the polymer, concentration of the polymer, nature of the aqueous medium present in the solution (notably salinity), temperature, etc. It can be expressed for example in Pa·s.

A viscosity measurement at a given shear rate can be performed for example by using a rotational viscometer with a cone and plate, parallel plates or cup and bob (coaxial cylinders) geometry. This measurement consists in measuring the torque required to rotate, at a given angular velocity, an object immersed in the fluid or in contact with the fluid. Through the calculation of a form factor which depends on the specific dimensions of the used geometry, torque is converted to shear stress and angular velocity to converted in shear rate.

The viscosity is the ratio between the shear stress and the shear rate. A value of viscosity is thus obtained from the torque measurement at each angular velocity. Some viscometers work in deformation, meaning that a shear rate is applied and the corresponding torque is measured, while other viscometers impose the shear stress (torque) and the shear rate is measured. The graph "Viscosity" vs. "Shear rate" is called a flow curve.

Figure 2:
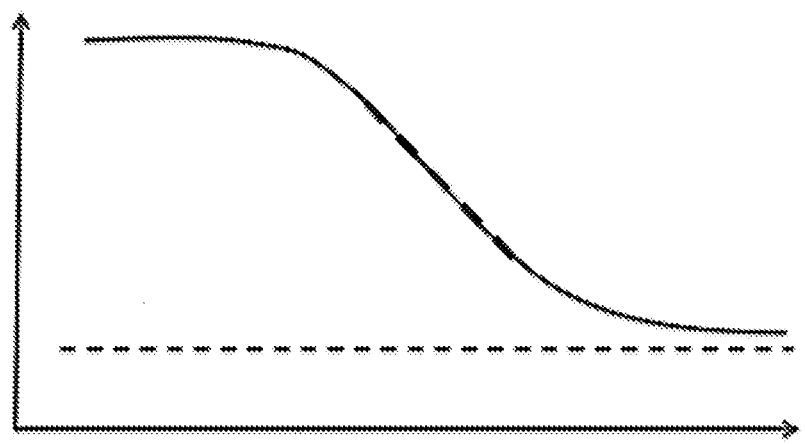
FIG. 2 shows a typical graph of the dynamic viscosity $\eta$ of a polymer as a function of the shear rate $\dot{\gamma}$. The dynamic viscosity can be read on the Y-axis and the shear rate can be read on the X-axis.

The typical aspect of such a flow curve for a given polymer solution is shown in FIG. 2.

At low shear rate, the curve has a first plateau meaning that viscosity does not depends on shear rate; the fluid is said to have a "Newtonian behavior". The value of the viscosity at this plateau is called "zero-shear rate viscosity" $\eta_0$.

Starting at a given shear rate which depends on all the physicochemical conditions previously listed, the viscosity $\eta$ starts to decrease with shear rate $\dot{\gamma}$ and follows a power law of the form $\eta = K \dot{\gamma}^{(x-1)}$ where K is the flow consistency index and x is the flow behavior index. Both K and x depend on all the physicochemical conditions previously listed.

At a high shear rate, the curve reaches a second plateau. In this area, the viscosity $\eta$ of the polymer solution approaches the viscosity of the aqueous solution devoid of polymer, $\eta_s$.

Practically, a flow curve is measured by applying a given shear rate to the solution and waiting until a constant viscosity value is measured by the viscometer. Once this value is obtained, the shear rate is changed and a new equilibrium value is measured.

Overall, viscosity as a function of shear rate approximately follows the following Carreau equation: $\eta = \eta_s + (\eta_0 - \eta_s) \cdot [1 + (\lambda \cdot \dot{\gamma})^2]^{(n-1)/2}$, wherein $\dot{\gamma}$ is the shear rate (for example expressed in s$^{-1}$), $\lambda$ is the relaxation time (for example expressed in s) and n is the Carreau coefficient which is close to the flow behavior index x of the power law equation. Parameters $\lambda$ and n depend on a number of factors related to physicochemical conditions (temperature, polymer concentration, nature and molecular weight of the polymer, salinity of the aqueous medium etc.). $\lambda$ roughly corresponds to the inverse of the shear rate at which viscosity starts to decrease with the shear rate.

The "specific viscosity at zero shear rate" $\eta_{sp}$ is defined as $\eta_{sp} = (\eta_0 - \eta_s)/\eta_s$ wherein $\eta_0$ is the zero-shear rate viscosity and $\eta_s$ is the viscosity of the aqueous solution devoid of polymer (in the same conditions and particularly at the same temperature). It is a dimensionless parameter.

The "intrinsic viscosity" of the polymer is defined as the limit of the specific viscosity at zero shear rate divided by the mass concentration of the polymer in the solution, when said mass concentration approaches zero. It can be expressed for instance in L/g. It represents in fact the effective volume under which 1 gram of polymer in solution counters the flow of liquid. The intrinsic viscosity of the polymer is characteristic of a given polymer combined with a given aqueous solution since it depends on polymer/polymer and polymer/solvent interactions. It slightly varies according to the temperature.

The present method of determining the intrinsic viscosity $[\eta]$ of the polymer solution at temperature T comprises a step of providing a single universal relation $R_1$ between (i), the product of polymer concentration C and intrinsic viscosity $[\eta]$, namely $C \cdot [\eta]$, and (ii) specific viscosity at zero shear rate $\eta_{sp}$.

The single universal relation $R_1$ may be obtained by:
providing one or more acrylamide-based polymers (for example having different natures and/or different molecular weights);
providing one or more aqueous media (for example having different salinities within the range of 6 to 250 g/L);
providing a number of acrylamide-based polymers;
preparing polymer solutions by dissolving the one or more polymers in the one or more aqueous media, at various concentrations;
for each polymer solution, performing measurements of the dynamic viscosity at various shear rates, and at a certain temperature;
deriving the specific viscosity at zero shear rate of each polymer solution, at this temperature, from said measurements; and then deriving the intrinsic viscosity of the polymer solution, at a given temperature; so as to obtain a set of specific viscosity at zero shear rate data associated with product of intrinsic viscosity and polymer concentration data;
providing a mathematical fit for the specific viscosity at zero shear rate data as a function of the product of intrinsic viscosity and polymer concentration data.

The acrylamide-based polymers which are provided preferably have different molecular weight distributions.

Preferably, at least some of the acrylamide-based polymers which are provided have been degraded from a higher molecular weight to a lower molecular weight, using mechanical devices such as mixers, rotor stators or valves.

In the above, the specific viscosity at zero shear rate $\eta_{sp}$ of each polymer solution, at each temperature, is derived from the measurements of the low shear viscosity $\eta_0$ through the formula $\eta_{sp} = (\eta_0 - \eta_s)/\eta_s$.

In the above, the intrinsic viscosity of each polymer solution, at each temperature, is obtained by plotting specific viscosity $\eta_{sp}$ divided by concentration C and extrapolating at zero concentration. The ordinate of such extrapolation is the intrinsic viscosity of the polymer/solvent system. Such method is based on the Huggins equation $\eta_{sp}=C\cdot[\eta]+k_H\cdot[\eta]^2\cdot C^2$ where C is the polymer concentration and $k_H$ the Huggins constant which depends on the polymer/solvent system.

Preferably, in the above steps, several different polymers (including preferably polymers with different degrees of degradation) are used as well as several different aqueous media (having different salinities) and several temperatures, so as to ensure that the set of data better represents the diversity of possible polymer solutions.

FIG. 1 provides an example of such a set of data, obtained with polymers including copolymers of acrylamide and sodium acrylate, copolymers of acrylamide and 2-acrylamide-2-methylpropane sulfonate, terpolymers of acrylamide, sodium acrylate and 2-acrylamide-2-methylpropane sulfonate, at different salinities (ranging from 6 to 257 g/L), at various temperatures (ranging from 25° C. to 90° C.) and at various polymer concentrations (ranging from 30 to 17500 ppm) at different degradation levels using a mixer.

The single universal relation $R_1$ may thus be defined as a mathematical fit for the data of FIG. 1 such as:

$$R_1: \eta_{sp}=C\cdot[\eta]+0.56(C\cdot[\eta])^{2.17}+0.0026(C\cdot[\eta])^{4.72}$$

Of course, it is also possible to define $R_1$ as a slightly different fit based on the same data.

Therefore, $R_1$ may also be defined as any other function where $\eta_{sp}$ deviates from $C\cdot[\eta]+0.56(C\cdot[\eta])^{2.17}+0.0026(C\cdot[\eta])^{4.72}$ at any value of $C\cdot[\eta]$ by less than 20%, preferably by less than 10%, more preferably by less than 5%, most preferably by less than 2% or even by less than 1%.

If $R_1$ is determined based on a different set of data from the data of FIG. 1, it may be defined as a slightly different function, but again, in preferred embodiments, $\eta_{sp}$ deviates from $C\cdot[\eta]+0.56(C\cdot[\eta])^{2.17}+0.0026(C\cdot[\eta])^{4.72}$ at any value of $C\cdot[\eta]$ by less than 20%, preferably by less than 10%, more preferably by less than 5%, most preferably by less than 2% or even by less than 1%.

The method for determining the intrinsic viscosity $[\eta]$ of a given polymer solution comprises a step of performing a measurement of the dynamic viscosity of the polymer solution at (at least) one polymer concentration $C_1$, at temperature T and at various shear rates, so as to deduce the zero-shear viscosity $\eta_0$ of the polymer solution at polymer concentration $C_1$ and at temperature T (as described above) and then the specific viscosity at zero shear rate $\eta_{sp}$.

According to some embodiments, a single measurement of the dynamic viscosity of the polymer solution at various shear rates is performed, so that a single specific viscosity at zero shear rate $\eta_{sp}$ at polymer concentration $C_1$ and at temperature T is determined.

The intrinsic viscosity $[\eta]$ of the polymer solution at temperature T is then directly determined by applying universal relation $R_1$ to this single specific viscosity at zero shear rate $\eta_{sp}$.

According to other embodiments, more than one measurements of the dynamic viscosity of the polymer solution at various shear rates are performed at at least two polymer concentrations $C_1$, $C_2$ (etc.) at temperature T.

In this case, the specific viscosity at zero shear rate $\eta_{sp}$ of the polymer solution is determined at the plurality of polymer concentration $C_1$, $C_2$ (etc.) and at temperature T. Then, the intrinsic viscosity $[\eta]$ is adjusted so as to obtain the best fit of specific viscosities at $C_1$, $C_2$ with the universal relation $R_1$, for instance using the method of least squares.

Using a single flow curve "viscosity vs. shear rate" measurement at a single polymer concentration makes the determination of the intrinsic viscosity easier and quicker.

Using several viscosity vs. shear measurements at various polymer concentrations may make the determination of the intrinsic viscosity more accurate and reliable.

Accuracy can be increased by performing different individual measurements in the same conditions (i.e. at the same polymer concentration $C_1$).

Method for Determining the Dynamic Viscosity of a Polymer Solution at a Polymer Concentration C' and at a Temperature T, Based on Measurements Performed at Temperature T but at (One or more) Polymer Concentrations other than C'

Based on the intrinsic viscosity of the polymer solution at temperature T, determined as described above, the dynamic viscosity of the polymer solution at this temperature T and at any shear rate and at any concentration can in turn be determined.

As a result, based on a single or a few viscosity vs. shear rate measurements, either at a single polymer concentration C1 or at at least two polymer concentrations $C_1$, $C_2$ (etc.), the viscosity of the polymer solution as a function of shear rate may be directly calculated at any given polymer concentration C', and still at temperature T.

This method thus comprises a step of providing a single universal relation $R_2$ between (i) the product of polymer concentration and intrinsic viscosity $C\cdot[\eta]$ and (ii) the Carreau coefficient n. The single universal relation $R_2$ may be obtained by:

providing one or more acrylamide-based polymers (for example having different natures and/or different molecular weights);

providing one or more aqueous media (for example having different salinities within the range of 6 to 250 g/L);

providing a number of acrylamide-based polymers;

preparing polymer solutions by dissolving the one or more polymers in the one or more aqueous media, at various concentrations;

for each polymer solution, performing several measurements of dynamic viscosity at various shear rates and at a certain temperature;

deriving the intrinsic viscosity of each polymer solution, at each temperature, from said measurements; deriving the Carreau coefficient n of each polymer solution at each polymer concentration and temperature from said measurements, so as to obtain a set of Carreau coefficient data associated with product of intrinsic viscosity and polymer concentration data;

providing a mathematical fit for the Carreau coefficient data as a function of the product of intrinsic viscosity and polymer concentration data.

The acrylamide-based polymers which are provided preferably have different molecular weight distributions.

Preferably, at least some of the acrylamide-based polymers which are provided have been degraded from a higher molecular weight to a lower molecular weight, using mechanical devices such as mixers, rotor stators or valves.

In the above, the intrinsic viscosity of each polymer solution, at each temperature, is derived from the measurements by extrapolating the specific viscosity at zero shear rate divided by polymer concentration vs. polymer concentration at zero polymer concentration. Alternatively, it can be determined by applying universal relation $R_1$ to the specific viscosity at zero shear rate and polymer concentration data.

In the above, the Carreau coefficient n of each polymer solution, at each polymer concentration and temperature, is derived from the measurements by fitting the viscosity vs. shear rate data to the Carreau equation $\eta=\eta_s+(\eta_0-\eta_s)\cdot[1+(\lambda\cdot\dot\gamma)^2]^{(n-1)/2}$. $\eta_0$ corresponds to viscosity at zero shear rate, $\eta_s$ is the solvent viscosity (which depends on temperature and salinity), and $\lambda$ and n are two adjustable parameters obtained by the method of least squares. Preferably, in the above steps, several different polymers are used as well as several different aqueous media (having different salinities) and different temperatures so as to ensure that the set of data better represents the diversity of possible polymer solutions.

The set of data used for generating universal relation $R_2$ may optionally be obtained from the same measurements as those from which the set of data used for generating universal relation $R_1$ are obtained. Alternatively, different measurements may be used for generating universal relation $R_1$ and universal relation $R_2$.

Figure 3:
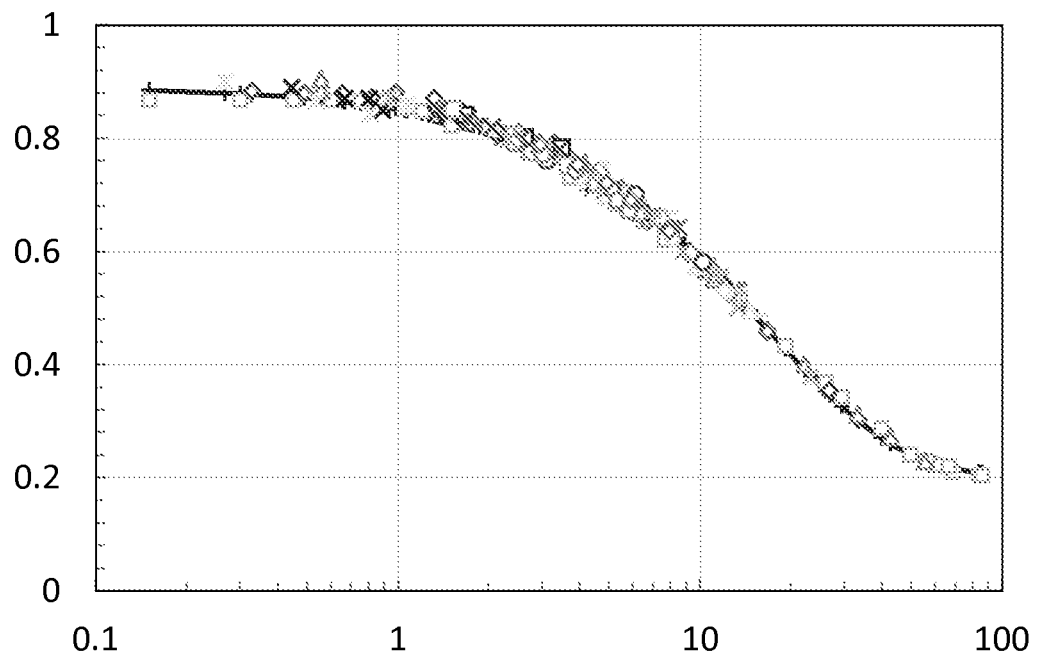
FIG. 3 shows the Carreau coefficient n as a function of the product of the polymer concentration and the intrinsic viscosity, for a large number of samples. The dimensionless Carreau coefficient can be read on the Y-axis and the dimensionless product of the polymer concentration and the intrinsic viscosity can be read on the X-axis.

FIG. 3 provides an example of a set of data used for obtaining universal relation $R_2$, generated with polymers including copolymers of acrylamide and sodium acrylate, copolymers of acrylamide and 2-acrylamide-2-methylpropane sulfonate, terpolymers of acrylamide, sodium acrylate and 2-acrylamide-2-methylpropane sulfonate, at different salinities (ranging from 6 to 257 g/L), at various temperatures (ranging from 25° C. to 90° C.) and at various polymer concentrations (ranging from 30 to 17500 ppm) at different degradation levels using a mixer.

The single universal relation $R_2$ may thus be defined as a mathematical fit for the data of FIG. 3 such as:

$$R_2: n=1-(0.796-0.687\times\exp(-0.059\times C\cdot[\eta])$$

Of course, it is also possible to defined $R_2$ as a slightly different fit based on the same data.

Therefore, the single universal relation $R_2$ may also be defined as any other function where n deviates from $1-(0.796-0.687\times\exp(-0.059\times C\cdot[\eta])$ at any value of $C\cdot[\eta]$ by less than 20%, preferably by less than 10%, more preferably by less than 5%, most preferably by less than 2% or even by less than 1%.

If $R_2$ is determined based on a different set of data from the data of FIG. 3, it may be defined as a slightly different function, but again, in preferred embodiments n deviates from $1-(0.796-0.687\times\exp(-0.059\times C\cdot[\eta])$ at any value of $C\cdot[\eta]$ by less than 20%, preferably by less than 10%, more preferably by less than 5%, most preferably by less than 2% or even by less than 1%.

The method for determining the dynamic viscosity of the polymer solution as a function of shear rate at temperature T and at a polymer concentration C' also comprises a step of providing a single universal relation $R_3$ between (i) the product of polymer concentration and intrinsic viscosity $C\cdot[\eta]$ and (ii) the ratio of relaxation time to diluted regime-relaxation time $\lambda/\lambda_d$. The single universal relation $R_3$ may obtained by:
  providing one or more acrylamide-based polymers (for example having different natures and/or different molecular weights);
  providing one or more aqueous media (for example having different salinities within the range of 6 to 250 g/L);
  providing a number of acrylamide-based polymers;
  preparing polymer solutions by dissolving the one or more polymers in the one or more aqueous media, at various concentrations;
  for each polymer solution, performing several measurements of the dynamic viscosity at various shear rates, at a given temperature;
  deriving the intrinsic viscosity of each polymer solution, at each temperature, from said measurements; deriving the relaxation time $\lambda$ of each polymer solution at each polymer concentration and temperature from said measurements; and deriving the diluted regime-relaxation time $\lambda_d$ at each temperature from said measurements; so as to obtain a set of relaxation time-to-diluted regime-relaxation time ratio data associated with product of intrinsic viscosity and polymer concentration data;
  providing a mathematical fit for the relaxation time-to-diluted regime-relaxation time ratio data as a function of the product of intrinsic viscosity and polymer concentration data.

The acrylamide-based polymers which are provided preferably have different molecular weight distributions.

Preferably, at least some of the acrylamide-based polymers which are provided have been degraded from a higher molecular weight to a lower molecular weight, using mechanical devices such as mixers, rotor stators or valves.

In the above, the intrinsic viscosity of each polymer solution, at each temperature, is derived from the measurements by extrapolating the specific viscosity at zero shear rate divided by polymer concentration vs. polymer concentration at zero polymer concentration (polymer concentration approaching zero). Alternatively, it can be determined by applying universal relation $R_1$ to the specific viscosity at zero shear rate and polymer concentration data.

In the above, the relaxation time $\lambda$ of each polymer solution, at each polymer concentration and temperature, is derived from the measurements by fitting the viscosity vs. shear rate data to the Carreau equation $\eta=\eta_s+(\eta_0-\eta_s)\cdot[1+(\lambda\cdot\dot\gamma)^2]^{(n-1)/2}$ where $\eta_0$ corresponds to viscosity at zero shear rate, $\eta_s$ is the solvent viscosity (which depends on temperature and salinity), and $\lambda$ and n are two adjustable parameters obtained by the method of least squares.

For values close to the diluted regime ($C[\eta]<1$), the relaxation time $\lambda$ becomes independent from polymer concentration. We call this relaxation time in the diluted regime $\lambda_d$.

In the above, the diluted regime-relaxation time $\lambda_d$ of each polymer solution, at each temperature, is derived from the measurements by plotting the relaxation time $\lambda$ as a function of polymer concentration, and by extrapolating the relaxation time at low polymer concentration (polymer concentration approaching zero).

Preferably, in the above steps, several different polymers are used as well as several different aqueous media (having different salinities) and different temperatures so as to ensure that the set of data better represents the diversity of possible polymer solutions.

The set of data used for generating universal relation $R_3$ may optionally be obtained from the same measurements as those from which the set of data used for generating universal relation $R_1$ are obtained. Alternatively, different measurements may be used for generating universal relation $R_3$ and universal relation $R_1$.

The set of data used for generating universal relation $R_3$ may optionally be obtained from the same measurements as those from which the set of data used for generating universal relation $R_2$ are obtained. Alternatively, different measurements may be used for generating universal relation $R_3$ and universal relation $R_2$.

Figure 4:
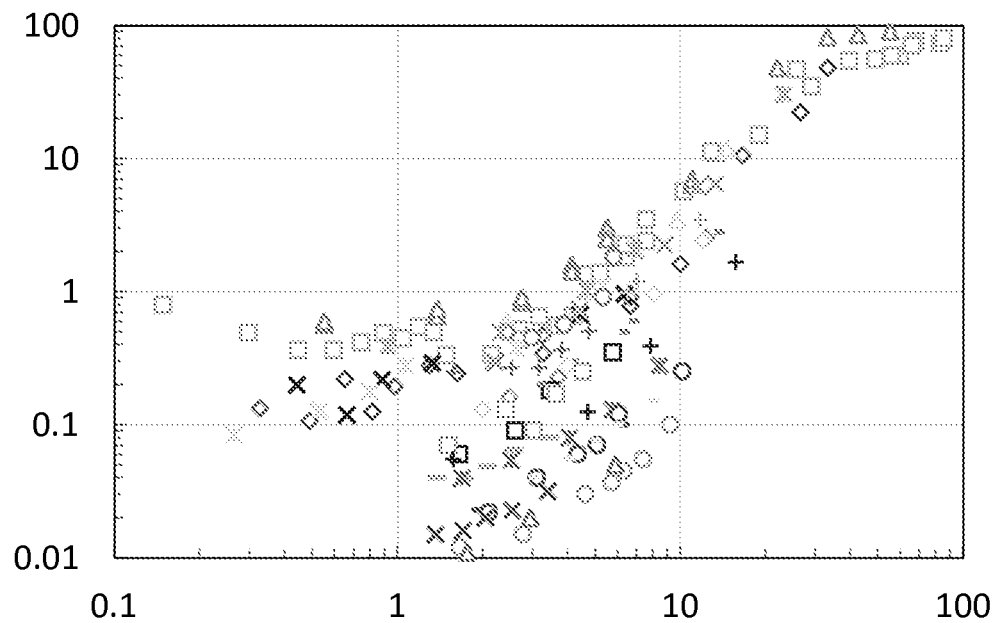
FIG. 4 shows the relaxation time as a function of the product of the polymer concentration and the intrinsic viscosity, for a large number of samples. Different symbols correspond to different samples. The relaxation time (expressed in s) can be read on the Y-axis and the dimensionless product of the polymer concentration and the intrinsic viscosity can be read on the X-axis.

FIG. 4 provides an example of a set of relaxation time λ data vs. product of intrinsic viscosity and polymer concentration C·[η] data obtained with polymers including copolymers of acrylamide and sodium acrylate, copolymers of acrylamide and 2-acrylamide-2-methylpropane sulfonate, terpolymers of acrylamide, sodium acrylate and 2-acrylamide-2-methylpropane sulfonate, at different salinities (ranging from 6 to 257 g/L), at various temperatures (ranging from 25° C. to 90° C.) and at various polymer concentrations (ranging from 30 to 17500 ppm) at different degradation levels using a mixer.

It can be readily seen that, for each polymer solution at a certain temperature, the relaxation time plateaus at low C·[η], which makes it possible to determine by extrapolation the diluted regime-relaxation time $\lambda_d$.

Figure 5:
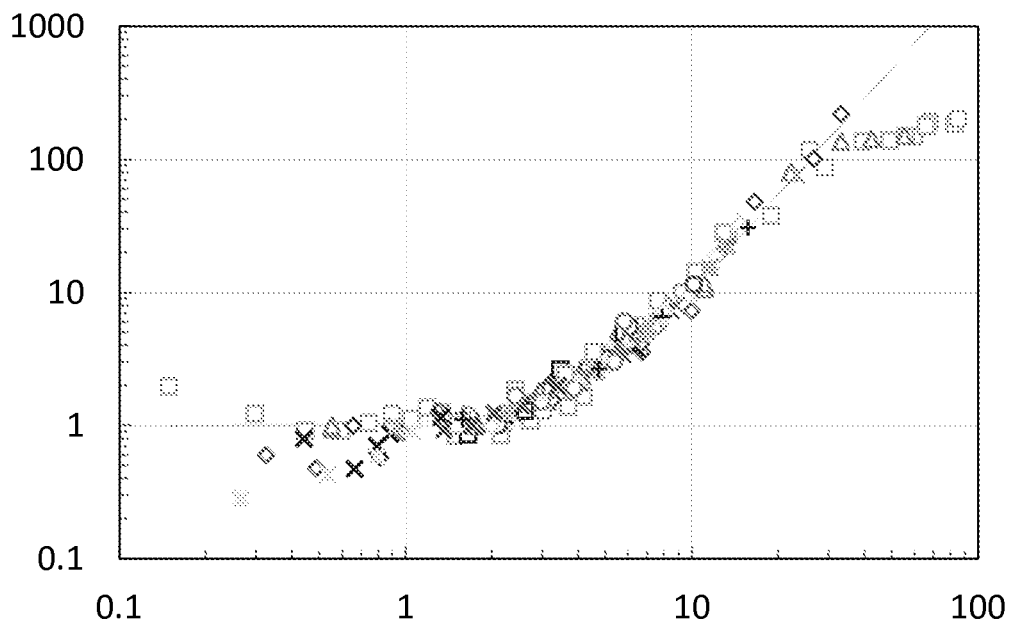
FIG. 5 shows the ratio of relaxation time to diluted-regime relaxation time $\lambda/\lambda_d$ as a function of the product of the polymer concentration and the intrinsic viscosity, for a large number of samples. The dimensionless ratio of relaxation time to diluted-regime relaxation time can be read on the Y-axis and the dimensionless product of the polymer concentration and the intrinsic viscosity can be read on the X-axis.

FIG. 5 then provides an example of a set of relaxation time-to-diluted regime-relaxation time ratio $\lambda/\lambda_d$ data as a function of the product of intrinsic viscosity and polymer concentration C·[η] data obtained with the same measurements as those used in FIG. 4.

The single universal relation $R_3$ may thus be defined as a fit for the data of FIG. 5 such as:

$$R_3: \lambda/\lambda_d = 1 + 0.04(C \cdot [\eta])^{2.4}$$

Of course, it is also possible to defined $R_3$ as a slightly different fit based on the same data.

Therefore, $R_3$ may also be defined as any other function where $\lambda/\lambda_d$ deviates from $1+0.04(C \cdot [\eta])^{2.4}$ at any value of C·[η] by less than 20%, preferably by less than 10%, more preferably by less than 5%, most preferably by less than 2% or even by less than 1%.

If $R_3$ is determined based on a different set of data from the data of FIG. 5, it may be defined as a slightly different function, but again, in preferred embodiments $\lambda/\lambda_d$ deviates from $1+0.04(C \cdot [\eta])^{2.4}$ at any value of C·[η] by less than 20%, preferably by less than 10%, more preferably by less than 5%, most preferably by less than 2% or even by less than 1%.

The method for determining the dynamic viscosity of the polymer solution as a function of shear rate at temperature T and at a polymer concentration C' comprises a step of determining the intrinsic viscosity [η] of this polymer solution at temperature T according to the method for determining the intrinsic viscosity described above. In this case, the one or more measurements of the dynamic viscosity of the aqueous polymer solution used for determining the intrinsic viscosity is/are performed at one or more polymer concentrations other than C' in the range 1<C·[η]<10.

According to FIG. 1, at C·[η]=1, we have $\eta_{sp} \approx 1.5$. At C·[η]=10, we have $\eta_{sp} \approx 230$. According to the definition of the specific viscosity $\eta_{sp}$, this implies that viscosity at zero shear rate $\eta_0$ of any polymer solution at any temperature will range between 2.5 and 231 times the solvent viscosity $\eta_s$.

Preferentially, the one or more measurements is/are performed in the range 2<C·[η]<5, corresponding to 5.6<$\eta_s$<30, as viscometers are usually more accurate and reliable for determining the whole flow curve in this viscosity range.

Thus, the viscosity at lower or higher concentrations may be determined based one or more measurements in the preferred concentration ranges.

For a given concentration C and at temperature T, the intrinsic viscosity is first determined by applying universal relation $R_1$ to the specific viscosity obtained from the viscosity at zero shear rate. Knowing the product C·[η], the shear thinning index n is determined by applying universal relation $R_2$, and the ratio $\lambda/\lambda_d$ is determined by applying universal relation $R_3$. $\lambda_d$ is obtained by adjusting the parameter λ so as to fit e.g. by the least squares method the flow curve determined experimentally. This determination can be performed at a single concentration or at several concentrations $C_1, C_2, \ldots$ for which all the flow curves will be fitted with one adjustable parameter $\lambda_d$.

Advantageously, the same measurements are used for determining the intrinsic viscosity [η] of the polymer solution at temperature T and the diluted regime-relaxation time $\lambda_d$ of the polymer solution at stake, at temperature T.

If a single measurement, at polymer concentration $C_1$ and temperature T, is used, then:
  The intrinsic viscosity [η] of the polymer solution at temperature T is determined by applying universal relation $R_1$ to the specific viscosity obtained from the viscosity at zero shear rate.
  The shear thinning index n is determined by applying universal relation $R_2$.
  The relaxation time $\lambda_1$ of the polymer at polymer concentration $C_1$ and temperature T is determined, by fitting the measured viscosity vs. shear rate data to the Carreau equation $\eta = \eta_s + (\eta_0 - \eta_s) \cdot [1 + (\lambda \cdot \dot{\gamma})^2]^{(n-1)/2}$.
  The diluted regime-relaxation time $\lambda_d$ is estimated by applying universal relation $R_3$ to the determined relaxation time $\lambda_1$, polymer concentration $C_1$ and the determined intrinsic viscosity [η] at temperature T.
  The relaxation time λ' of the polymer solution at temperature T and polymer concentration C' is estimated by applying back universal relation $R_3$ to the estimated diluted-regime relaxation time $\lambda_d$, polymer concentration C' and the determined intrinsic viscosity [η] at temperature T.
  The Carreau coefficient n' of the polymer solution at temperature T and polymer concentration C' is estimated by applying universal relation $R_2$ to polymer concentration C' and intrinsic viscosity [η] at temperature T.
  The specific viscosity at zero shear rate $\eta_{sp}'$ of the polymer solution at polymer concentration C' and at temperature T is estimated by applying universal relation $R_1$ to the intrinsic viscosity [η] at temperature T and polymer concentration C'.
  The zero-shear viscosity $\eta_0'$ of the polymer solution at polymer concentration C' and at temperature T is estimated as $\eta_0' = \eta_s \cdot (\eta_{sp}' + 1)$.
  The dynamic viscosity η' of the polymer solution as a function of shear rate $\dot{\gamma}$, at temperature T and at polymer concentration C', is estimated by applying again the Carreau equation: $\eta' = \eta_s + (\eta_0' - \eta_s) \cdot [1 + (\lambda' \cdot \dot{\gamma})^2]^{(n'-1)/2}$.

If at least two measurements, at polymer concentrations $C_1, C_2$, etc. and temperature T, are used, the same steps are performed except that the diluted regime-relaxation time $\lambda_d$ is determined as an average based on the simultaneous fit of all the flow curves by one single $\lambda_d$ value. The best fit is e.g. obtained through the method of least squares.

Using a single viscosity vs. shear measurement at a single polymer concentration makes the entire method easier and quicker.

Using several viscosity vs. shear measurements at various polymer concentrations may render the method more accurate or reliable.

Averaging may also be performed in a similar manner based on different individual measurements in the same conditions (i.e. at the same polymer concentration C).

Method for Determining the Dynamic Viscosity of a Polymer Solution at a Polymer Concentration C' and at a Temperature T', Based on Measurements Performed at Different Temperature T and at (One or more) Polymer Concentrations The method described above for determining the intrinsic viscosity of a polymer solution at a given temperature can be repeated several times at different temperatures, so as to determine the dependence of the intrinsic viscosity of the polymer solution as a function of temperature.

Figure 6:
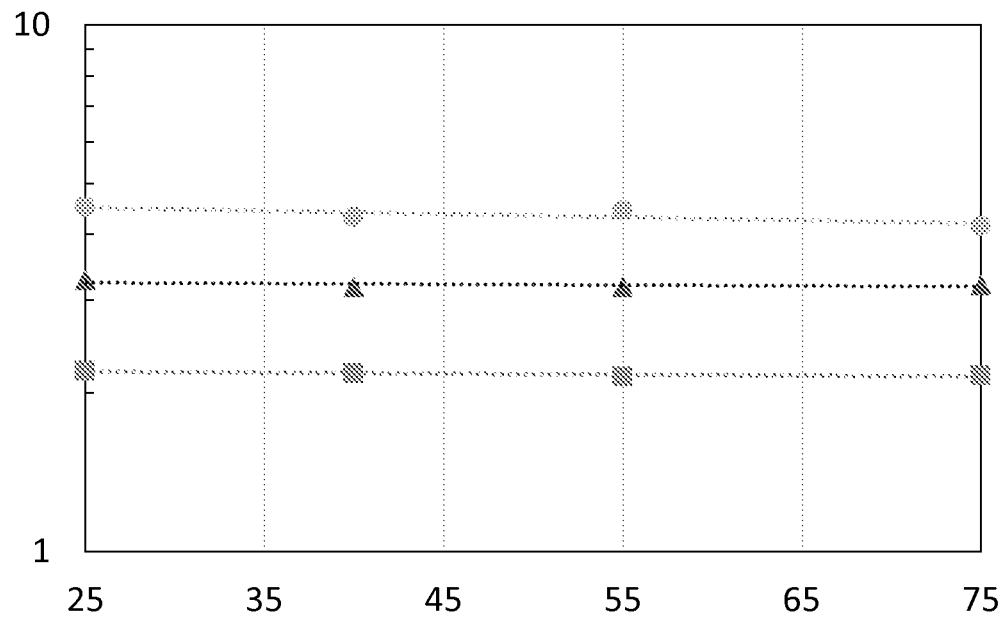
FIG. 6 shows the intrinsic viscosity as a function of temperature, for three different polymer solutions (which differ in the molecular weight of the polymer). The intrinsic viscosity (in L/g) can be read on the Y-axis and the temperature (in ° C.) can be read on the X-axis.

An example is illustrated in FIG. 6, for three different polymers having respective molecular weights of 5.8, 10 and 15.4 MDa.

Based on such a graph, it is then possible to evaluate (without performing any further measurement) the intrinsic viscosity of a polymer solution at any given temperature, and in particular at a temperature T' at which no measurement data is available, for example by fitting the data with a power law or exponential law.

It then becomes possible to determine the dynamic viscosity at zero shear rate of the polymer solution at this temperature T' and at any concentration—based on measurements performed at a different temperature T.

More specifically, the intrinsic viscosity [η] of the polymer solution at temperature T' is evaluated based on a mathematical fit applied to data corresponding to determined intrinsic viscosity [η] of the polymer solution at a plurality of temperatures T other than T' (as illustratively shown in FIG. 6).

The method described above for determining the diluted-regime relaxation time of a polymer solution at a given temperature can be repeated several times at different temperatures, so as to determine the dependence of the diluted-regime relaxation time of the polymer solution as a function of temperature.

Figure 7:
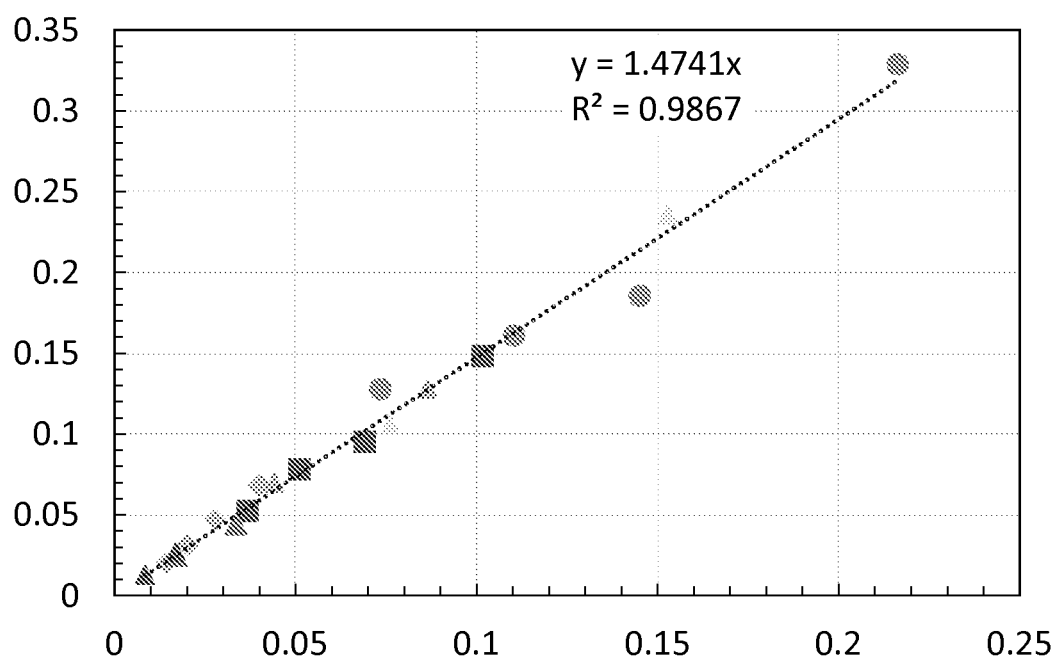
FIG. 7 shows the diluted-regime relaxation time $\lambda_d$ (on the Y-axis, in s) for polymers having different molecular weights, as a function of $\eta_s \times [\eta] \times M/T$ (on the X-axis) where $\eta_s$ is the viscosity of the solvent, $[\eta]$ is the intrinsic viscosity of the polymer solution, M is the viscosimetric molecular weight of the polymer and Y is the temperature.

An example is illustrated in FIG. 7 for the same three different polymers having respective molecular weights of 5.8, 10 and 15.4 MDa, at different temperatures and salinities. The diluted-regime relaxation time follows a universal law $R_4$.

$R_4$ may be defined as a mathematical fit for the data of FIG. 7 such as:

$$R_4: \lambda_d = 1.474 \times \eta_s \times [\eta] \times M/T$$

Of course, it is also possible to define $R_4$ as a slightly different fit based on the same data.

Therefore, $R_4$ may also be defined as any other function where $\lambda_d$ deviates from $1.474 \times \eta_s \times M/T$ at any value of $\eta_s$, [η], M and T by less than 20%, preferably by less than 10%, more preferably by less than 5%, most preferably by less than 2% or even by less than 1%.

If $R_4$ is determined based on a different set of data from the data of FIG. 7, it may be defined as a slightly different function, but again, in preferred embodiments, $\lambda_d$ deviates from $1.474 \times \eta_s \times M/T$ at any value of $\eta_s$, [η], M and T by less than 20%, preferably by less than 10%, more preferably by less than 5%, most preferably by less than 2% or even by less than 1%.

From the knowledge of $\lambda_d$ at temperature T, $\lambda_d$ at temperature T' can be predicted from $R_4$ as follows, using relation $R_5$:

$$R_5: \lambda_d(T') = \lambda_d(T) \times (\eta_s(T') \times [\eta](T') \times T)/(\eta_s(T) \times [\eta](T) \times T')$$

Where [η](T') is the intrinsic viscosity at temperature T' and $\eta_s$(T') is the solvent viscosity at T'.

If a single measurement, at polymer concentration $C_1$ and temperature T, is used, then:

The relaxation time $\lambda_1$ of the polymer at polymer concentration $C_1$ and temperature T is determined, by fitting the measured viscosity vs. shear rate data to the Carreau equation $\eta = \eta_s + (\eta_0 - \eta_s) \cdot [1 + (\lambda \cdot \dot{\gamma})^2]^{(n-1)/2}$.

The diluted regime-relaxation time $\lambda_d$ is estimated by applying universal relation $R_3$ to the determined relaxation time $\lambda_1$, polymer concentration $C_1$ and the determined intrinsic viscosity [η] at temperature T.

The diluted regime-relaxation time $\lambda_d$ at temperature T' is calculated by applying relation $R_5$, based diluted regime-relaxation time $\lambda_d$ at temperature T and intrinsic viscosity [η] at temperature T' evaluated as described above.

The relaxation time $\lambda'$ of the polymer solution at temperature T' and polymer concentration C' is estimated by applying relation $R_3$ to the estimated diluted-regime relaxation time $\lambda_d$ at temperature T', polymer concentration C' and the intrinsic viscosity [η] at temperature T' evaluated as described above.

The Carreau coefficient n' of the polymer solution at temperature T' and polymer concentration C' is estimated by applying universal relation $R_2$ to polymer concentration C' and intrinsic viscosity [η] at temperature T' evaluated as described above.

The specific viscosity at zero shear rate $\eta_{sp}'$ of the polymer solution at polymer concentration C' and at temperature T' is estimated by applying universal relation $R_1$ to the intrinsic viscosity [η] at temperature T' evaluated as described above, and polymer concentration C'.

The zero-shear viscosity $\eta_0'$ of the polymer solution at polymer concentration C' and at temperature T' is estimated as $\eta_0' = \eta_s \cdot (\eta_{sp}' + 1)$.

The dynamic viscosity $\eta'$ of the polymer solution as a function of shear rate $\dot{\gamma}$, at temperature T' and at polymer concentration C', is estimated by applying again the Carreau equation: $\eta' = \eta_s + (\eta_0' - \eta_s) \cdot [1 + (\lambda' \cdot \dot{\gamma})^2]^{(n'-1)/2}$.

If at least two measurements, at polymer concentrations $C_1$, $C_2$, etc. and temperature T, are used, the same steps are performed except that the diluted regime-relaxation time $\lambda_d$ is determined as an average based on at least two estimates. This is similar to what has already been described above.

Method for Determining the Molecular Weight

By determining the intrinsic viscosity of the polymer solution, as described above, the determination of the (unknown) viscosimetric molecular weight of the polymer becomes possible. By molecular weight is herein meant the average viscosimetric molecular weight which lies between the number-average molecular weight Mn and the weight-average molecular weight Mw.

Indeed, the molecular weight of the polymer can be estimated by using universal relation R4: $M = (\lambda_d \cdot T)/([\eta] \cdot \eta_s)/1.474$, where [η] and $\eta_s$ are considered at temperature T.

The intrinsic viscosity of the polymer solution at temperature T and the diluted-regime relaxation time $\lambda_d$ of the polymer solution at temperature T may be determined as already described in detail above, based on a single or a few viscosity vs. shear rate measurements, either at a single polymer concentration C1 or at at least two polymer concentrations $C_1$, $C_2$, etc.

This makes it possible to determine the molecular weight M of the polymer based on said single or few viscosity vs. shear rate measurements, without knowing the polymer type/composition (provided it is an acrylamide based polymer) and the brine composition.

The invention claimed is:

1. A method for determining intrinsic viscosity [η] of an aqueous polymer solution at a temperature T, wherein the aqueous polymer solution comprises at least one acrylamide-based polymer in an aqueous solvent, the aqueous solvent having a salinity of from 6 to 250 g/L, the method comprising:
   providing a single universal relation $R_1$ between (i), product of polymer concentration and intrinsic viscosity C·[η], and (ii) specific viscosity at zero shear rate $\eta_{sp}$;
   performing a measurement of dynamic viscosity of the aqueous polymer solution at one polymer concentration $C_1$, at temperature T and at various shear rates;
   determining from said measurement zero-shear viscosity $\eta_0$ of the aqueous polymer solution at polymer concentration $C_1$ and at temperature T;
   calculating specific viscosity at zero shear rate of the aqueous polymer solution at polymer concentration $C_1$ and at temperature T as $\eta_{sp}=(\eta_0-\eta_s)/\eta_s$, where $\eta_s$ is zero-shear viscosity of the aqueous solvent; and
   estimating the intrinsic viscosity [η] of the aqueous polymer solution at temperature T by applying the universal relation $R_1$ to the calculated specific viscosity at zero shear rate $\eta_{sp}$ and polymer concentration $C_1$.

2. The method according to claim 1, wherein one or more measurements of the dynamic viscosity of the aqueous polymer solution at various shear rates are performed only at the polymer concentration $C_1$.

3. The method according to claim 1, further comprising:
   performing a measurement of dynamic viscosity of the aqueous polymer solution, at at least another polymer concentration $C_2$, at temperature T, and at various shear rates;
   determining zero-shear viscosity $\eta_0$ of the aqueous polymer solution at least the polymer concentrations $C_1$ and $C_2$ and at temperature T, from the measurement of the dynamic viscosity of the aqueous polymer solution at the polymer concentration $C_1$ and the measurement of the dynamic viscosity of the aqueous polymer solution at the polymer concentration $C_2$;
   calculating specific viscosity at zero shear rate of the aqueous polymer solution at least the polymer concentrations $C_1$ and $C_2$ and at temperature T as $\eta_{sp}=(\eta_0-\eta_s)/\eta_s$, where $\eta_s$ is the zero-shear viscosity of the aqueous solvent; and
   estimating an average intrinsic viscosity [η] of the aqueous polymer solution at temperature T by fitting the calculated specific viscosity at zero shear rate of the aqueous polymer solution at least the polymer concentrations $C_1$ and $C_2$ and at temperature T with the universal relation $R_1$.

4. The method according to claim 1, wherein the single universal relation $R_1$ is obtained by:
   providing a number of acrylamide-based polymers;
   for each acrylamide-based polymer, performing several measurements of dynamic viscosity of aqueous solutions of the acrylamide-based polymer in an aqueous solvent, the aqueous solvent having a salinity of from 6 to 250 g/L, at various shear rates and various polymer concentrations, at one or several temperatures;
   deriving specific viscosity at zero shear rate and intrinsic viscosity of each aqueous solution, at each concentration and temperature, from said several measurements, so as to obtain a set of specific viscosity at zero shear rate data associated with product of intrinsic viscosity and polymer concentration data; and
   providing a mathematical fit for the specific viscosity at zero shear rate data as a function of the product of intrinsic viscosity and polymer concentration data.

5. The method according to claim 1, wherein the single universal relation $R_1$ is defined as $\eta_{sp}=C\cdot[\eta]+0.56 (C\cdot[\eta])^{2.17}+0.0026 (C\cdot[\eta])^{4.72}$ or as any other function where $\eta_{sp}$ deviates from $C\cdot[\eta]+0.56 (C\cdot[\eta])^{2.17}+0.0026 (C\cdot[\eta])^{4.72}$ at any value of $C\cdot[\eta]$ by less than 20%.

6. A method for determining dynamic viscosity of an aqueous polymer solution as a function of shear rate, at a temperature T and at a polymer concentration C', wherein the aqueous polymer solution comprises at least one acrylamide-based polymer in an aqueous solvent, the aqueous solvent having a salinity of from 6 to 250 g/L, the method comprising:
   providing a single universal relation $R_2$ between (i) product of polymer concentration and intrinsic viscosity C·[η] and (ii) Carreau coefficient n;
   providing a single universal relation $R_3$ between (i) the product of polymer concentration and intrinsic viscosity C·[η] and (ii) ratio of relaxation time to diluted regime-relaxation time $\lambda/\lambda_d$;
   determining intrinsic viscosity [η] of the aqueous polymer solution at temperature T by:
      providing a single universal relation $R_1$ between (i), the product of polymer concentration and intrinsic viscosity C·[η], and (ii) specific viscosity at zero shear rate $\eta_{sp}$;
      performing a measurement of dynamic viscosity of the aqueous polymer solution at one or more polymer concentrations other than C', at temperature T and at various shear rates;
      determining from said measurement zero-shear viscosity $\eta_0$ of the aqueous polymer solution at the one or more polymer concentrations other than C' and at temperature T;
      calculating specific viscosity at zero shear rate of the aqueous polymer solution at the one or more polymer concentrations other than C' and at temperature T as $\eta_{sp}=(\eta_0-\eta_s)/\eta_s$, where $\eta_s$ is zero-shear viscosity of the aqueous solvent; and
      estimating the intrinsic viscosity [η] of the aqueous polymer solution at temperature T by applying the universal relation $R_1$ to the calculated specific viscosity at zero shear rate $\eta_{sp}$ and the one or more polymer concentrations other than C';
   estimating diluted regime-relaxation time $\lambda_d$ of the aqueous polymer solution at temperature T by:
      determining relaxation time $\lambda_1$ of the aqueous polymer solution at temperature T and at a single polymer concentration $C_1$, from a measurement of dynamic viscosity of the aqueous polymer solution at polymer concentration $C_1$ and at temperature T, and then applying the universal relation $R_3$ to the determined relaxation time $\lambda_1$, polymer concentration $C_1$ and the determined intrinsic viscosity [η] at temperature T; or
      determining at least two relaxation times $\lambda_1$ and $\lambda_2$ of the aqueous polymer solution at temperature T and at at least two respective polymer concentrations $C_1$ and $C_2$, from respective measurements of dynamic viscosity of the aqueous polymer solution at the at least two polymer concentrations $C_1$ and $C_2$ and at temperature T, and applying the universal relation $R_3$ to the at least two determined relaxation times $\lambda_1$ and $\lambda_2$, respective polymer concentrations $C_1$ and $C_2$ and the determined intrinsic viscosity [η] at temperature T so as to provide an average value of $\lambda_d$ at temperature T;

estimating relaxation time λ' of the aqueous polymer solution at temperature T and polymer concentration C' by applying the universal relation $R_3$ to the estimated diluted-regime relaxation time $\lambda_d$, the polymer concentration C' and the determined intrinsic viscosity [η] at temperature T;

estimating Carreau coefficient n' of the aqueous polymer solution at temperature T and polymer concentration C' by applying the universal relation $R_2$ to polymer concentration C' and the determined intrinsic viscosity [η] at temperature T;

estimating specific viscosity at zero shear rate $\eta_{sp}'$ of the aqueous polymer solution at polymer concentration C' and at temperature T by applying the universal relation $R_1$ to (i) the determined intrinsic viscosity [η] at temperature T and (ii) polymer concentration C';

estimating a zero-shear viscosity $\eta_0'$ of the aqueous polymer solution at polymer concentration C' and at temperature T as $\eta_0' = \eta_s \cdot (\eta_{sp}' + 1)$; and estimating the dynamic viscosity η' of the aqueous polymer solution as a function of shear rate $\dot{\gamma}$, at temperature T and at polymer concentration C' by applying Carreau's equation: $\eta' = \eta_s + (\eta_0' - \eta_s) \cdot [1 + (\lambda' \cdot \dot{\gamma})^2]^{(n'-1)/2}$.

7. The method according to claim 6, wherein the single universal relation $R_2$ is obtained by:

providing a number of acrylamide-based polymers;

for each acrylamide-based polymer, performing several measurements of dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving a Carreau coefficient and intrinsic viscosity of each aqueous solution, at each concentration and temperature, from said several measurements, so as to obtain a set of Carreau coefficient data associated with product of intrinsic viscosity and polymer concentration data; and providing a mathematical fit for the Carreau coefficient data as a function of the product of intrinsic viscosity and polymer concentration data.

8. The method according to claim 6, wherein the single universal relation $R^2$ is defined as $n = 1 - (0.796 - 0.687 \times \exp(-0.059 \times C \cdot [\eta]))$ or as any other function where n deviates from $1 - (0.796 - 0.687 \times \exp(-0.059 \times C \cdot [\eta]))$ at any value of $C \cdot [\eta]$ by less than 20%.

9. The method according to claim 6, wherein the single universal relation $R_3$ is obtained by:

providing a number of acrylamide-based polymers;

for each acrylamide-based polymer, performing several measurements of dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving relaxation time, diluted regime-relaxation time and intrinsic viscosity of each aqueous solution, at each concentration and temperature, from said several measurements, so as to obtain a set of relaxation time-to-diluted regime-relaxation time ratio data associated with product of intrinsic viscosity and polymer concentration data; and providing a mathematical fit for the relaxation time-to-diluted regime-relaxation time ratio data as a function of the product of intrinsic viscosity and polymer concentration data.

10. The method according to claim 6, wherein the single universal relation $R^3$ is defined as $\lambda/\lambda_d = 1 + 0.04 (C \cdot [\eta])^{2.4}$ or as any other function where $\lambda/\lambda_d$ deviates from $1 + 0.04 (C \cdot [\eta])^{2.4}$ at any value of $C \cdot [\eta]$ by less than 20%.

11. The method of claim 6, wherein each measurement of the dynamic viscosity of the aqueous polymer solution is performed at one or more polymer concentrations C such that $C \cdot [\eta]$ is within the range of 1 to 10 and $C' \cdot [\eta]$ is out of the range of 1 to 10.

12. A method for determining dynamic viscosity of an aqueous polymer solution as a function of shear rate, at a temperature T' and at a polymer concentration C', wherein the aqueous polymer solution comprises at least one acrylamide-based polymer in an aqueous solvent, the aqueous solvent having a salinity of from 6 to 250 g/L, the method comprising:

providing a single universal relation $R_2$ between (i) product of polymer concentration and intrinsic viscosity $C \cdot [\eta]$ and (ii) Carreau coefficient n;

providing a single universal relation $R_3$ between (i) the product of polymer concentration and intrinsic viscosity $C \cdot [\eta]$ and (ii) ratio of relaxation time to diluted regime-relaxation time $\lambda/\lambda_d$;

determining intrinsic viscosity [η] of the aqueous polymer solution at a plurality of temperatures different from T', wherein each determination of the intrinsic viscosity is performed by:

providing a single universal relation $R_1$ between (i), the product of polymer concentration and intrinsic viscosity $C \cdot [\eta]$, and (ii) specific viscosity at zero shear rate $\eta_{sp}$;

performing a measurement of dynamic viscosity of the aqueous polymer solution at the polymer concentration $C_1$, at a given temperature from amongst the plurality of temperatures different from T' and at various shear rates;

determining from said measurement zero-shear viscosity $\eta_0$ of the aqueous polymer solution at polymer concentration $C_1$ and at the given temperature;

calculating specific viscosity at zero shear rate of the aqueous polymer solution at polymer concentration $C_1$ and at the given temperature as $\eta_{sp} = (\eta_0 - \eta_s)/\eta_s$, where $\eta_s$ is zero-shear viscosity of the aqueous solvent; and estimating the intrinsic viscosity [η] of the aqueous polymer solution at the given temperature by applying the universal relation $R_1$ to the calculated specific viscosity at zero shear rate $\eta_{sp}$ and polymer concentration $C_1$;

evaluating intrinsic viscosity [η] of the aqueous polymer solution at temperature T' based on the determined intrinsic viscosity [η] of the aqueous polymer solution at the plurality of temperatures, by a mathematical fit;

estimating diluted regime-relaxation time $\lambda_d$ of the aqueous polymer solution at one or more temperatures T from amongst the plurality of temperatures by:

determining relaxation time $\lambda_1$ of the aqueous polymer solution at a temperature T, from amongst the one or more temperatures, and at the polymer concentration $C_1$, from the measurement of the dynamic viscosity of the aqueous polymer solution at polymer concentration $C_1$ and at said temperature T, and then applying the universal relation $R_3$ to the determined relaxation time $\lambda_1$, polymer concentration $C_1$ and the determined intrinsic viscosity $[\eta]$ at this temperature T; or determining at least two relaxation times $\lambda_1$ and $\lambda_2$ of the aqueous polymer solution at temperature T and at at least two respective polymer concentrations $C_1$ and $C_2$, from respective measurements of dynamic viscosity of the aqueous polymer solution at the at least two polymer concentrations $C_1$ and $C_2$ and at temperature T, and applying the universal relation $R_3$ to the at least two determined relaxation times $\lambda_1$ and $\lambda_2$, respective polymer concentrations $C_1$ and $C_2$ and the determined intrinsic viscosity $[\eta]$ at temperature T so as to provide an average value of $\lambda_d$ at temperature T;

estimating the diluted regime-relaxation time $\lambda_d$ of the aqueous polymer solution at temperature T' as:

$$\lambda_d(T') \times (\eta_s(T') \times [\eta](T') \times T') / (\eta_s(T) \times [\eta](T) \times T)$$

where $\lambda_d(T)$ is the diluted regime-relaxation time $\lambda_d$ of the aqueous polymer solution at temperature T, $\eta_s(T')$ and $\eta_s(T)$ are respectively zero-shear viscosities of the aqueous solvent at temperatures T' and T, and $[\eta](T')$ and $[\eta](T)$ are respectively intrinsic viscosities of the aqueous polymer solution at temperatures T' and T;

estimating relaxation time $\lambda'$ of the aqueous polymer solution at temperature T' and polymer concentration C' by applying the universal relation $R_3$ to the estimated diluted regime-relaxation time $\lambda_d$ at temperature T', the polymer concentration C' and the evaluated intrinsic viscosity $[\eta]$ at temperature T';

estimating Carreau coefficient n' of the aqueous polymer solution at temperature T' and polymer concentration C' by applying the universal relation $R_2$ to polymer concentration C' and the evaluated intrinsic viscosity $[\eta]$ at temperature T';

estimating specific viscosity at zero shear rate $\eta_{sp}'$ of the aqueous polymer solution at polymer concentration C' and at temperature T' by applying the universal relation $R_1$ to (i) the evaluated intrinsic viscosity $[\eta]$ at temperature T' and (ii) polymer concentration C';

estimating zero-shear viscosity $\eta_0'$ of the aqueous polymer solution at polymer concentration C' and at temperature T'=$\eta_0'$=$\eta_s \cdot (\eta_{sp}'+1)$; and estimating the dynamic viscosity $\eta'$ of the aqueous polymer solution as a function of shear rate $\gamma$, at temperature T' and at polymer concentration C' by applying Carreau's equation: $\eta' = \eta_{s+} (\eta_0' - \eta_s) \cdot [1 + (\lambda' \cdot \gamma)^2]^{(n'-1)/2}$.

13. The method according to claim 12, wherein the single universal relation $R_2$ is obtained by:

providing a number of acrylamide-based polymers;

for each acrylamide-based polymer, performing several measurements of dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving a Carreau coefficient and intrinsic viscosity of each aqueous solution, at each concentration and temperature, from said several measurements, so as to obtain a set of Carreau coefficient data associated with product of intrinsic viscosity and polymer concentration data; and providing a mathematical fit for the Carreau coefficient data as a function of the product of intrinsic viscosity and polymer concentration data.

14. The method according to claim 12, wherein the single universal relation $R_2$ is defined as $n=1-(0.796-0.687\times\exp(-0.059\times C \cdot [\eta]))$ or as any other function where n deviates from $1-(0.796-0.687\times\exp(-0.059\times C \cdot [\eta]))$ at any value of $C \cdot [\eta]$ by less than 20%.

15. The method according to claim 12, wherein the single universal relation $R_3$ is obtained by:

providing a number of acrylamide-based polymers;

for each acrylamide-based polymer, performing several measurements of dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving relaxation time, diluted regime-relaxation time and intrinsic viscosity of each aqueous solution, at each concentration and temperature, from said several measurements, so as to obtain a set of relaxation time-to-diluted regime-relaxation time ratio data associated with product of intrinsic viscosity and polymer concentration data; and providing a mathematical fit for the relaxation time-to-diluted regime-relaxation time ratio data as a function of the product of intrinsic viscosity and polymer concentration data.

16. The method according to claim 12, wherein the single universal relation $R_3$ is defined as $\lambda/\lambda_d = 1 + 0.04 (C \cdot [\eta])^{2.4}$ or as any other function where $\lambda/\lambda_d$ deviates from $1 + 0.04 (C \cdot [\eta])^{2.4}$ at any value of $C \cdot [\eta]$ by less than 20%.

17. A method for determining viscosimetric molecular weight of an acrylamide-based polymer, the method comprising:

providing an aqueous polymer solution, the aqueous polymer solution comprising the acrylamide-based polymer in an aqueous solvent, the aqueous solvent having a salinity of from 6 to 250 g/L;

providing a single universal relation $R_3$ between (i) product of polymer concentration and intrinsic viscosity $C \cdot [\eta]$ and (ii) ratio of relaxation time to diluted regime-relaxation time $\lambda/\lambda_d$;

determining intrinsic viscosity $[\eta]$ of the aqueous polymer solution at a temperature T by:

providing a single universal relation $R_1$ between (i), product of polymer concentration and intrinsic viscosity $C \cdot [\eta]$, and (ii) specific viscosity at zero shear rate $\eta_{sp}$;

performing a measurement of dynamic viscosity of the aqueous polymer solution at one polymer concentration $C_1$, at temperature T and at various shear rates;

determining from said measurement zero-shear viscosity $\eta_0$ of the aqueous polymer solution at polymer concentration $C_1$ and at temperature T;

calculating specific viscosity at zero shear rate of the aqueous polymer solution at polymer concentration $C_1$ and at temperature T as $\eta_{sp} = (\eta_0 - \eta_s)/\eta_s$, where $\eta_s$ is zero-shear viscosity of the aqueous solvent; and estimating the intrinsic viscosity $[\eta]$ of the aqueous polymer solution at temperature T by applying the universal relation $R_1$ to the calculated specific viscosity at zero shear rate $\eta_{sp}$ and polymer concentration $C_1$;

estimating diluted regime-relaxation time $\lambda_d$ of the aqueous polymer solution at temperature T by:

determining relaxation time $\lambda_1$ of the aqueous polymer solution at temperature T and polymer concentration $C_1$, from the measurement of the dynamic viscosity of the aqueous polymer solution at polymer concentration $C_1$ and at temperature T, and then applying the universal relation $R_3$ to the determined relaxation time $\lambda_1$, polymer concentration $C_1$ and the determined intrinsic viscosity $[\eta]$ at temperature T; or determining at least two relaxation times $\lambda_1$ and $\lambda_2$ of the aqueous polymer solution at temperature T and at at least two respective polymer concentrations $C_1$ and $C_2$, from respective measurements of dynamic viscosity of the aqueous polymer solution at the at least two polymer concentrations $C_1$ and $C_2$ and at temperature T, and applying the universal relation $R_3$ to the at least two determined relaxation times $\lambda_1$ and $\lambda_2$, respective polymer concentrations $C_1$ and $C_2$ and the determined intrinsic viscosity $[\eta]$ at temperature T so as to provide an average value of $\lambda_d$ at temperature T;

estimating the viscosimetric molecular weight of the polymer according to the equation $M=(\lambda_d \cdot T)/([\eta]\cdot\eta_s)/1.474$ where $\eta_s$ is the zero-shear viscosity of the aqueous solvent at temperature T.

18. The method according to claim 17, wherein the single universal relation $R_3$ is obtained by:

providing a number of acrylamide-based polymers;

for each acrylamide-based polymer, performing several measurements of dynamic viscosity of aqueous solutions of the acrylamide-based polymer in an aqueous solvent, the aqueous solvent having a salinity of from 6 to 250 g/L, at various shear rates and various polymer concentrations, at one or several temperatures;

deriving relaxation time, diluted regime-relaxation time and intrinsic viscosity of each aqueous solution, at each concentration and temperature, from said several measurements, so as to obtain a set of relaxation time-to-diluted regime-relaxation time ratio data associated with product of intrinsic viscosity and polymer concentration data; and providing a mathematical fit for the relaxation time-to-diluted regime-relaxation time ratio data as a function of the product of intrinsic viscosity and polymer concentration data.

19. The method according to claim 17, wherein the single universal relation $R_3$ is defined as $\lambda/\lambda_d=1+0.04\,(C\cdot[\eta])^{2.4}$ or as any other function where $\lambda/\lambda_d$ deviates from $1+0.04\,(C\cdot[\eta])^{2.4}$ at any value of $C\cdot[\eta]$ by less than 20%.

20. The method of claim 1, wherein the at least one acrylamide-based polymer comprises units derived from one or more monomers selected from acrylamide, sodium acrylate, N-vinyl pyrrolidone and 2-acrylamide-2-methylpropane sulfonate.

* * * * *

UNITED STATES PATENT AND TRADEMARK OFFICE
CERTIFICATE OF CORRECTION

| | | |
|---|---|---|
| PATENT NO. | : 11,841,302 B2 | Page 1 of 1 |
| APPLICATION NO. | : 17/432009 | |
| DATED | : December 12, 2023 | |
| INVENTOR(S) | : Stéphane Jouenne and Bertrand Levache | |

It is certified that error appears in the above-identified patent and that said Letters Patent is hereby corrected as shown below:

In the Claims

In Claim 12, Column 25, Line 45, delete "T'=" and insert -- T' as --.

Signed and Sealed this
Thirtieth Day of January, 2024

Katherine Kelly Vidal
*Director of the United States Patent and Trademark Office*